(12) United States Patent
Stratford et al.

(10) Patent No.: US 7,306,625 B1
(45) Date of Patent: Dec. 11, 2007

(54) BALLOON EXPANDABLE STENT

(75) Inventors: Peter William Stratford, Surrey (GB);
Alistair Stewart Taylor, Surrey (GB);
Vincent James O'Byrne, Surrey (GB);
John Tom Clarke, Co. Mayo (IE);
Denis Dominic Healy, Galway (IE)

(73) Assignee: Abbott Laboratories, Abbott Park, IL (US)

( * ) Notice: Subject to any disclaimer, the term of this patent is extended or adjusted under 35 U.S.C. 154(b) by 912 days.

(21) Appl. No.: 10/018,783

(22) PCT Filed: Jun. 26, 2000

(86) PCT No.: PCT/GB00/02485

§ 371 (c)(1),
(2), (4) Date: Jun. 12, 2002

(87) PCT Pub. No.: WO01/00109

PCT Pub. Date: Jan. 4, 2001

(30) Foreign Application Priority Data

Jun. 24, 1999 (EP) .................................. 99304975

(51) Int. Cl.
*A61F 2/06* (2006.01)

(52) U.S. Cl. ..................... 623/1.46; 427/2.24

(58) Field of Classification Search ............... 623/1.11, 623/1.12, 1.44, 1.46, 1.47, 1.48, 3.28; 606/191–198; 427/2.21, 2.24, 421

See application file for complete search history.

(56) References Cited

U.S. PATENT DOCUMENTS

| | | | |
|---|---|---|---|
| 5,344,426 A | 9/1994 | Lau et al. | |
| 5,674,276 A | 10/1997 | Andersen et al. | |
| 5,830,217 A | 11/1998 | Ryan | |
| 5,876,445 A | 3/1999 | Andersen et al. | |
| 5,899,935 A | 5/1999 | Ding | |
| 5,997,517 A * | 12/1999 | Whitbourne | 623/901 |
| 6,168,602 B1 | 1/2001 | Ryan | |
| 6,273,910 B1 * | 8/2001 | Limon | 623/1.15 |
| 6,673,105 B1 * | 1/2004 | Chen | 623/1.15 |
| 6,673,107 B1 * | 1/2004 | Brandt et al. | 623/1.35 |

FOREIGN PATENT DOCUMENTS

| | | |
|---|---|---|
| EP | 0 680 278 B1 | 1/1999 |
| EP | 0 920 843 A1 | 6/1999 |
| WO | WO 93/01221 | 1/1993 |
| WO | WO 94/01056 | 1/1994 |
| WO | WO 98/30615 | 7/1998 |

\* cited by examiner

*Primary Examiner*—Kevin T. Truong
(74) *Attorney, Agent, or Firm*—Sughrue Mion, PLLC

(57) ABSTRACT

The present invention relates to a balloon expandable stent mounted on a balloon catheter, the entire assembly being overcoated with a coherent polymer coating, which is preferably substantially continuous over the circumference and, more preferably, axial length of the stent on the balloon. The polymer coating improves retention of the stent on the balloon during delivery and does not adversely effect the deployment characteristics, nor the balloon failure characteristics. The product is made by mounting the stent on the balloon and coating the assembly with a liquid coating composition containing a suitable polymer followed by curing of the coating. The polymer is biocompatible and preferably crosslinkable in the coating composition, and crosslinked in the final product. A suitable polymer is formed from monomers including a zwitterionic, preferably a phosphoryl choline, group, and monomers including a trialkoxysilyl group. Preferably the coated product is contacted with ethylene oxide to provide simultaneous sterilization and additional curing.

10 Claims, No Drawings

BALLOON EXPANDABLE STENT

The present invention relates to balloon expandable stents for delivering into body lumens, in particular to stents formed from tubes, especially metal tubes. In particular this invention relates to means for retaining the stent on the balloon during storage and delivery of the stent through the body lumen prior to deployment, without adversely effecting the balloon strength or deployment of the stent.

Balloon expandable stent, either made from wires, or made from metal tubes which are cut or etched to form openings in the surface are crimped onto the balloon delivery device either as part of the manufacturing/assembly process, or immediately prior to use by a surgeon. Generally the stent is positioned over the balloon, sometimes on a sleeve which is positioned over the balloon, and is then crimped down onto the balloon. During the delivery procedure, when the delivery catheter carrying the stent is being maneuvered through body lumens, the stent is subjected to forces which may dislodge the stent from its desired position on the balloon.

Means have been described for retaining the stent in position on the balloon during delivery. For instance protrusions have been provided on the balloon, or the catheter near to the balloon, having shoulders above and/or below the stent location which bear against the stent when it is subjected to an axial force. Alternatively protrusions may be provided on the external surface of the balloon, or on a sleeve located between the stent and the balloon, which protrude into the holes through the wall of the stent. Again these protrusions have shoulders which may bear against the axially directed surfaces of those holes. However the procedures used to make such balloons tend to lead to weakening of the balloon wall and/or increase in the pressure required to inflate the balloon and/or require additional manufacturing steps and steps for careful positioning of the stent upon the balloon.

Other methods have involved the application of an adhesive layer between the stent and the balloon. However such layers may have an adverse effect on balloon strength and/or inflation characteristics. Furthermore it is difficult to ensure a good interfacial contact between the stent and the adhesive and/or adhesive and balloon. Such adhesives may also have an adverse effect on biocompatibility.

Other solutions to this problem have involved providing an external sheath surrounding the balloon when mounted on the catheter which must be retracted prior to deployment of the stent. This involves an extra step in the delivery process, increases the external diameter of the stent/delivery device combination and increases the likelihood of mechanical failure of the delivery device.

The present invention seeks to solve the above problems. Some embodiments of the invention also improve the biocompatibility of the delivery device, and stent once delivered. Some embodiments of the invention may also provide improved lubricity of the delivery device during the stent delivery procedure.

In EP-A-0920843, a device is claimed which has a hydrogel coating on the external surface of an endoprosthesis for delivering a drug into the wall of a body lumen into which the prostheses is inserted. The prosthesis is for instance a stent. The stent may be coated when mounted on a balloon. The sole example of hydrogel is a polyacrylic acid hydrogel, which appears to be crosslinked using a polyisocyanate crosslinker. It appears that the film is not continuous around the exterior surface of the balloon/stent combination.

According to the invention there is provided a new kit comprising a balloon catheter comprising a balloon at or near its distal end, and a stent mounted on the balloon, characterized in that in that the exterior surface of the balloon and stent are provided with a coherent coating comprising a film-forming polymer.

In the invention the coating is preferably continuous around the exterior surface of the balloon/stent, over at least a portion of the axial extent of that section. Preferably the coating is provided along the entire axial length of the stent, most preferably being continuous around the circumference throughout the axial length. Preferably the coating extends beyond at least the distal stent end and preferably also the proximal stent end. It may extend along the exterior surface of the balloon catheter shaft proximal of the balloon.

The coating may comprise components other than the film forming polymer, for instance fillers, diluents, plasticisers, colouring agents, opacifying agents, pharmaceutically active agents, radioactive or other imaging agents etc. Often, however, the coating may consist essentially only of the film forming polymer.

The film forming polymer is preferably crosslinked to provide adequate coherent strength. Preferably the crosslinking of the polymer is achieved wholly or mainly after coating of the polymer on the surface which will be described in more detail in connection with the process below.

Preferably the polymer is biocompatible. Since the stent is primarily used in vascular lumens, the coating is preferably additionally hemo-compatible. The bio/hemo-compatibility should preferably persist during the delivery process and, preferably also, after the delivery process. Where the coating is biostable, that is not degraded after deployment of the device, the biocompatibility of the coating should persist throughout the period during which the coating remains on the stent surface after deployment.

The biocompatibility is preferably achieved by the use of a polymer having pendent zwitterionic groups. Suitable groups X are for instance as defined below as groups of general formula III, V or VII.

Preferably a polymer having zwitterionic moieties is formed from radical polymerization of ethylenically unsaturated monomers including a zwitterionic monomer. Alternatively condensation polymers or preformed polymers derivatised by reaction with zwitterionic derivatising reagents may be used.

Preferably the zwitterionic monomer has the general formula I:

$$YBX \hspace{4cm} I$$

wherein

B is a straight or branched alkylene (alkanediyl), alkyleneoxaalkylene or alkylene oligo-oxaalkylene chain optionally containing one or more fluorine atoms up to and including perfluorinated chains or, if X or Y contains a terminal carbon atom bonded to B, a valence bond;

X is a zwitterionic group; and

Y is an ethylenically unsaturated polymerisable group selected from

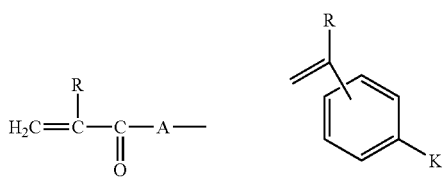

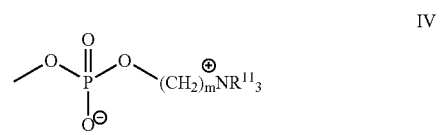

CH$_2$=C(R)—CH$_2$—O—, CH$_2$=C(R)—CH$_2$OC(O)—,
CH$_2$=C(R)OC(O)—, CH$_2$=C(R)—O—, CH$_2$=C(R)
CH$_2$OC(O)N(R$^1$)—, R$^2$OOCCR=CRC(O)—O—,
RCH=CHC(O)O—, RCH=C(COOR$^2$)CH$_2$—C(O)—
O—,

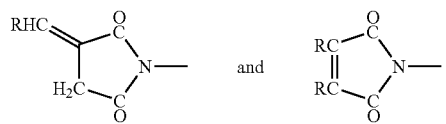

wherein:
R is hydrogen or a C$_1$-C$_4$ alkyl group;
R$^1$ is hydrogen or a C$_1$-C$_4$ alkyl group or R$^1$ is —B—X where B and X are as defined above; and
R$^2$ is hydrogen or a C$_{1-4}$ alkyl group;
A is —O— or —NR$^1$—;
K is a group —(CH$_2$)$_p$OC(O)—, —(CH$_2$)$_p$C(O)O—, —(CH$_2$)$_p$OC(O)O—, —(CH$_2$)$_p$NR$^3$—, —(CH$_2$)$_p$NR$^3$C(O)—, —(CH$_2$)$_p$C(O)NR$^3$—, —(CH$_2$)$_p$NR$^3$C(O)O—, —(CH$_2$)$_p$OC(O)NR$^3$—, —(CH$_2$)$_p$NR$^3$C(O)NR$^3$— (in which the groups R$^3$ are the same or different), —(CH$_2$)$_p$O—, —(CH$_2$)$_p$SO$_3$—, or, optionally in combination with B, a valence bond
p is from 1 to 12; and
R$^3$ is hydrogen or a C$_1$-C$_4$ alkyl group.
In the zwitterionic monomer the general formula I, the zwitterionic group preferably has the general formula III

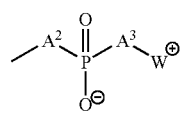

in which the moieties A$^2$ and A$^3$, which are the same or different, are —O—, —S—, —NH— or a valence bond, preferably —O—, and W$^+$ is a group comprising an ammonium, phosphonium or sulphonium cationic group and a group linking the anionic and cationic moieties which is preferably a C$_{1-12}$-alkanediyl group,
preferably in which W$^+$ is a group of formula —W$^1$—N$^+$R$^9$$_3$, —W$^1$—P$^+$R$^{10}$$_3$, —W$^1$—S$^+$R$^{10}$$_2$ or
—W$^1$—Het$^+$ in which:

W$^1$ is alkanediyl of 1 or more, preferably 2-6 carbon atoms optionally containing one or more ethylenically unsaturated double or triple bonds, disubstituted-aryl(arylene), alkylene arylene, arylene alkylene, or alkylene aryl alkylene, cycloalkanediyl, alkylene cycloalkyl, cycloalkyl alkylene or alkylene cycloalkyl alkylene, which group W$^1$ optionally contains one or more fluorine substituents and/or one or more functional groups; and either the groups R$^9$ are the same or different and each is hydrogen or alkyl of 1 to 4 carbon atoms, preferably methyl, or aryl, such as phenyl, or two of the groups R$^9$ together with the nitrogen atom to which they are attached form an aliphatic heterocyclic ring containing from 5 to 7 atoms, or the three groups R$^9$ together with the nitrogen atom to which they are attached form a fused ring structure containing from 5 to 7 atoms in each ring, and optionally one or more of the groups R$^9$ is substituted by a hydrophilic functional group, and the groups R$^{10}$ are the same or different and each is R$^9$ or a group OR$^9$, where R$^9$ is as defined above; or Het is an aromatic nitrogen-, phosphorus- or sulphur-, preferably nitrogen-, containing ring, for example pyridine.

Most preferably, the zwitterionic group of the formula III, has the general formula IV:

where the groups R$^{11}$ are the same or different and each is hydrogen or C$_{1-4}$ alkyl, and m is from 1 to 4, in which preferably the groups R$^{11}$ are the same preferably methyl.

Alternatively, the zwitterionic group may be a betaine group (ie in which the cation is closer to the backbone), for instance a sulpho-, carboxy- or phospho-betaine. A betaine group should have no overall charge and is preferably therefore a carboxy- or sulpho-betaine. If it is a phospho-betaine the phosphate terminal group must be a diester, i.e., be esterified with an alcohol. Such groups may be represented by the general formula V

—A$^4$—R$^{12}$—N(R$^{13}$)$_2$—R$^{14}$—V    V in which A$^4$ is a valence bond, —O—, —S— or —NH—, preferably —O—;
V is a carboxylate, sulphonate or phosphate diester (monovalently charged) anion;
R$^{12}$ is a valence bond (together with A$^4$) or alkanediyl, —C(O)alkylene- or —C(O)NHalkylene preferably alkanediyl, and preferably containing from 1 to 6 carbon atoms in the alkanediyl chain;
the groups R$^{13}$ are the same or different and each is hydrogen or alkyl of 1 to 4 carbon atoms or the groups R$^{13}$ together with the nitrogen to which they are attached form a heterocyclic ring of 5 to 7 atoms; and
R$^{14}$ is alkyanediyl of 1 to 20, preferably 1 to 10, more preferably 1 to 6 carbon atoms.

One preferred sulphobetaine monomer has the formula VI

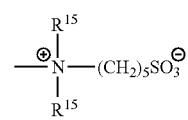

where the groups R$^{15}$ are the same or different and each is hydrogen or C$_{1-4}$ alkyl and s is from 2 to 4.

Preferably the groups R$^{15}$ are the same. It is also preferable that at least one of the groups R$^{15}$ is methyl, and more preferable that the groups R$^{15}$ are both methyl.

Preferably s is 2 or 3, more preferably 3.

Alternatively the zwitterionic group may be an amino acid moiety in which the alpha carbon atom (to which an amine group and the carboxylic acid group are attached) is joined through a linker group to the backbone of the biocompatible polymer. Such groups may be represented by the general formula VII

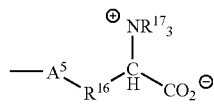

VII in which $A^5$ is a valence bond, —O—, —S— or —NH—, preferably —O—, $R^{16}$ is a valence bond (optionally together with $A^5$) or alkanediyl, —C(O)alkylene- or —C(O)NHalkylene, preferably alkanediyl and preferably containing from 1 to 6 carbon atoms; and the groups $R^{17}$ are the same or different and each is hydrogen or alkyl of 1 to 4 carbon atoms, preferably methyl, or two or three of the groups $R^{17}$, together with the nitrogen to which they are attached, form a heterocyclic ring of from 5 to 7 atoms, or the three group $R^{17}$ together with the nitrogen atom to which they are attached form a fused ring heterocyclic structure containing from 5 to 7 atoms in each ring.

Preferably the monomers used to form the polymer include a surface binding monomer having the general formula II $$Y^1R^4 \quad \quad \text{II}$$

wherein $Y^1$ is selected from

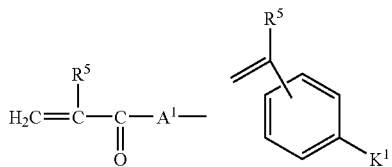

$CH_2=C(R^5)$—$CH_2$—O—, $CH_2=C(R^5)$—$CH_2$ OC(O)—, $CH_2=C(R^5)OC(O)$—, $CH_2=C(R^5)$—O—, $CH_2=C(R^5)$ $CH_2OC(O)N(R^6)$—, $R^7OOCCR^5=CR^5C(O)$—O—, $R^5CH=CHC(O)O$—, $R^5CH=C(COOR^7)CH_2$—C(O)—O—,

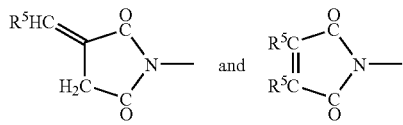

wherein:

$R^5$ is hydrogen or a $C_1$-$C_4$ alkyl group;
$R^6$ is hydrogen or a $C_1$-$C_4$ alkyl group or $R^6$ is $R^4$;
$R^7$ is hydrogen or a $C_{1-4}$ alkyl group;
$A^1$ is —O— or —$NR^6$—; and
$K^1$ is a group —$(CH_2)_qOC(O)$—, —$(CH_2)_qC(O)O$—, —$(CH_2)_qOC(O)O$—, —$(CH_2)_qNR^8$—, —$(CH_2)_qNR^8C(O)$—, —$(CH_2)_qC(O)NR^8$, —$(CH_2)_qNR^8C(O)O$—, —$(CH_2)_qOC(O)NR^8$—, —$(CH_2)_qNR^8C(O)NR^8$— (in which the groups $R^8$ are the same or different), —$(CH_2)_qO$—, —$(CH_2)_qSO_3$—, or a valence bond q is from 1 to 12;
and $R^8$ is hydrogen or a $C_1$-$C_4$ alkyl group;
and $R^4$ is a surface binding group, selected from hydrophobic groups, ionic groups, reactive groups capable of forming covalent bonds with surface functional groups on the surface of the tube and crosslinkable groups capable of forming intermolecular crosslinks, optionally in conjunction with curing agents.

In the binding monomer of the general formula II, the group $R^4$ is preferably a) a straight or branched alkyl, alkoxyalkyl or oligoalkoxyalkyl chain containing 6 or more, preferably 6 to 24 carbon atoms, unsubstituted or substituted by one or more fluorine atoms optionally containing one or more carbon double or triple bonds; or b) a siloxane group —$(CR^{18a}_2)_{qq}(SiR^{19}_2)(OSiR^{19}_2)_{pp}R^{19}$ in which each group $R^{18}$ is the same or different and is hydrogen or alkyl of 1 to 4 carbon atoms, or aralkyl, for example benzyl or phenethyl, each group $R^{19}$ is alkyl of 1 to 4 carbon atoms, qq is from 1 to 6 and pp is from 0 to 49; or c) a crosslinkable group, capable of reacting with the groups of the same definition, or with groups of a different definition provided by a mixture of monomers of the general formula II, having different groups $R^4$.

Preferred crosslinkable groups have the formula —$R^{20}Q$, where $R^{20}$ is a valence bond or, more preferably, a straight or branched alkanediyl, alkylenoxyalkylene or alkylene(oligooxyalkylene) group and Q is a reactive group selected from cinnamyl, epoxy, —CHOHCH$_2$Hal (in which Hal is a halogen atom), methylol, silyl and siloxyl groups containing one or more reactive substituents such as halogen, for example chlorine, or alkoxy, generally containing from 1 to 4 carbon atoms, for example methoxy or ethoxy, hydroxyl, amino, carboxyl, ethylenically acetylenically unsaturated crosslinkable groups, acetoacetoxy, chloroalkylsulphone, succinimido, tosylate, triflate, imidazolecarbonylamino or optionally substituted triazine groups.

Most preferred definitions of $R^4$ are $C_{1-18}$-alkyl, -alkenyl or -alkynyl, optionally including fluorine substituents, and mixtures of different groups —$R^{20}$—Q, in which the groups $R^{20}$ are the same or different and each represent $C_{2-6}$-alkanediyl, and one of the groups Q is hydroxyl and the other is a reactive silyl group, preferably having the formula Si(OR$^{22}$)$_3$, where each group $R^{22}$ is $C_{1-4}$-alkyl, preferably methyl or ethyl and n is 0 or 1. A suitable mixture of two comonomers of the formula II is of hydroxyalkylmethacrylate and trimethoxysilylalkyl methacrylate, preferably in which both alkanediyl groups $R^{20}$ are the same and are, most preferably, propyl. Preferably the monomers include hydrophobic surface binding group containing monomers and cross-linkable group containing monomers.

In monomers of the formula I and II, Y and $Y^1$ are preferably H$_2$C=C(R)C(O)A— and H$_2$C=C(R$^5$)C(O)A$^1$—, respectively. R and $R^5$ are preferably hydrogen or, more preferably, methyl. A and $A^1$ are preferably the same and are most preferably —O—.

B is preferably $C_{2-18}$, more preferably $C_{2-6}$,-alkanediyl, branched, or, preferably, straight chain, that is $(CH_2)_r$, where r is 2 to 18, preferably 2 to 6.

The ethylenically unsaturated monomers may include diluent monomers, for instance which may be added to adjust the solubility of the polymer in the coating composition from which it is coated, to adjust the hydrophilicity/phobicity, to control the flexibility of the coating, or for other reasons. Such monomers are generally non-ionic. Suitable diluent monomers are alkyl(alk)acrylates, for instance having 1 to 4 carbon atoms in the alkyl group, N-alkyl- or N,N-dialkyl(alk)acrylamides, for instance having 1 to 4 carbon atoms in the or each alkyl group, (alk)acrylamide, hydroxylalkyl(alk)acrylates, for instance having 1 to 6 carbon atoms in the alkyl group, vinyl lactams, such as vinylpyrrolidone, and styrene. Mixtures may be used.

The ethylenically unsaturated monomers from which the polymer having zwitterionic moieties is formed may include other functional monomers. For instance monomers having functional groups may provide attachment points for ligands such as pharmaceutically active agents, specific binding moieties, or antithrombogenic agents. Comonomers may alternatively include ionic groups, for instance for providing electrostatic attraction with counterionically charged moieties desired to be bonded to the coating. For instance cationic or cationisable monomers may allow loading of the zwitterionic polymer coating of the graft by anionically charged mucopolysaccharides such as heparin, which may reduce thrombogenicity of the graft still further.

Preferably the zwitterionic monomer is used in the monomer mixture in a molar proportion of at least 1%, preferably less than 75%, more preferably in the range 5 to 50%, most preferably 10-33%. The surface binding monomer is generally used in molar proportion of at least 2%, preferably at least 5% or at least 10%, more preferably in the range 15 to 99%. Where the surface binding monomers provide cross-linkability, the level of reactive cross-linkable groups is preferably in the range 5 to 33%. Where the surface binding monomer comprises hydrophobic physisorbable groups, it is preferably present in a molar amount in the range 50 to 99%, more preferably 60-95%.

In a particularly preferred embodiment of the invention the polymer used is as described in our co-pending application publication number WO-A-98130615.

Where the polymer is formed from monomer including reactive groups Q, in the kit of the invention, such groups have been reacted to provide covalent bonds to the underlying surface functional groups, and/or intermolecular and intramolecular crosslinking. It is particularly preferred in the invention that the monomers include crosslinkable groups Q and the in the novel kit, the polymer has been subjected to conditions whereby crosslinking has taken place. Crosslinking improves the coherent strength of the coating and hence the retention of the stent on the balloon.

The kit of the invention should be sterile or sterilizable. The kit may be provided in a closed package, and is preferably sterile within the package. Whilst sterilization maybe achievable by sterilizing the individual components, or by sterilizing the partially assembled device, for instance the balloon catheter/stent combination and, separately, the coating composition, preferably the coated kit is subjected to sterilization.

Sterilization maybe by subjecting the device to high temperature and pressures, for instance in an autoclave, by exposure to irradiation, or preferably, by treatment with ethylene oxide gas.

The present inventors have found that exposure of certain useful polymers to ethylene oxide gas may result in improvement in the function of the polymer to retain the stent on the balloon. Thus when the polymer having the preferred groups Q comprising reactive silyl groups of the formula $Si(OR^{22})_3$, contacting the polymer with ethylene oxide, before, during, after or instead of subjecting the polymer to any other crosslinking conditions, result in improved stent retention.

It is believed that polymers having pendent reactive silyl groups of the formula $Si(OR^{22})_3$ have not previously been contacted with gaseous ethylene oxide to provide curing of the polymer. According to a second aspect of the invention therefore there is provided a curing process in which a polymer having pendent groups of the formulae $Si(OR^{26})_3$, in which each group $R^{26}$ is independently selected from $C_{1-4}$-alkyl, is contacted with gaseous ethylene oxide to provide a cured polymer.

In this aspect of the invention, the silyl group is generally introduced by forming the polymer from ethylenically unsaturated monomers including a monomer of the formula VIII $$Y^2R^{30}Q^1 \qquad \qquad VIII$$

wherein
$Y^2$ is selected from

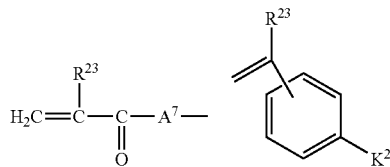

$CH_2\!=\!C(R^{23})\!-\!CH_2\!-\!O\!-\!$, $CH_2\!=\!C(R^{23})\!-\!CH_2OC(O)\!-\!$, $CH_2\!=\!C(R^{23})OC(O)\!-\!$, $CH_2\!=\!C(R^{23})\!-\!O\!-\!$, $CH_2\!=\!C(R^{23})CH_2OC(O)N(R^{24})\!-\!$, $R^{25}OOCCR^{23}\!=\!CR^{23}C(O)\!-\!O\!-\!$, $R^{23}CH\!=\!CHC(O)O\!-\!$, $R^{23}CH\!=\!C(COOR^{25})CH_2\!-\!C(O)\!-\!O\!-\!$,

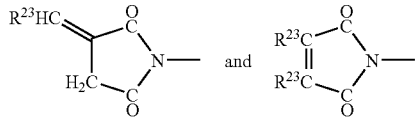

and wherein:
$R^{23}$ is hydrogen or a $C_1$-$C_4$ alkyl group;
$R^{24}$ is hydrogen or a $C_1$-$C_4$ alkyl group or $R^{24}$ is $R^{30}Q^1$;
$R^{25}$ is hydrogen or a $C_{1-4}$ alkyl group;
$A^7$ is —O— or —$NR^{24}$—; and
$K^2$ is a group —$(CH_2)_tOC(O)$—, —$(CH_2)_tC(O)O$—, —$(CH_2)_tOC(O)O$—, —$(CH_2)_tNR^{28}$—, —$(CH_2)_tNR^{28}C(O)$, —$(CH_2)_tC(O)NR^{28}$, —$(CH_2)_tNR^{28}C(O)O$—, —$(CH_2)_tOC(O)NR^{28}$—, —$(CH_2)_tNR^{28}C(O)NR^{28}$— (in which the groups $R^{28}$ are the same or different), —$(CH_2)_tO$—, —$(CH_2)_tSO_3$—, or a valence bond
t is from 1 to 12;
and $R^{28}$ is hydrogen or a $C_1$-$C_4$ alkyl group;
$R^{30}$ is a straight or branched $C_{2-24}$ alkanediyl group, or a alkylenoxaalkylene or alkylene(oligo-oxaalkylene) group in which each alkylene has 2 to 12 carbon atoms, and
$Q^1$ is a group $Si(OR^{26})_3$
the groups $R^{26}$ are independently selected from $C_{1-4}$alkyl groups.
Preferably each of the groups $R^{26}$ are $C_{1\ or\ 2}$-alkyl, most preferably methyl.

In groups $R^{30}$, an alkyleneoxealkylene or alkylene(oligo-oxaalkylene) group, has alkylene groups of 2 to 3 carbon atoms, most preferably 2 carbon atoms. Most preferably $R^{30}$ is an alkanediyl group, most preferably having 2 to 6 carbon atoms, most preferably 3 or 4 carbon atoms. Most preferably it is a group $(CH_2)_{2\ to\ 4}$-alkyl group.

Preferably the polymer is formed from ethylenically unsaturated monomers also including monomer of the formula I described above. The monomers preferably also include a monomer of the formula II above in which the group Q is a crosslinkable group of the formulae $R^{20}$ Q in which Q is a hydroxyl group. $R^{20}$ maybe any of the groups defined above for $R^{30}$.

Ethylene oxide contact is generally conducted under conditions used for sterilization procedures. For instance gas is contacted with the polymer for a period of at least an hour, more preferably at least 2 hours for instance up to 12 hours or even more, at a temperature of at least 40 C, more preferably at least 45 C up to 70 C, most preferably 45-55 C, optionally in the presence of steam and usually with a diluent, carrier gas of nitrogen or another inert gas. The proportion in the total gas of ethylene oxide is preferably at least 50%, more preferably at least about 80%. Treatment may conveniently be carried out under reduce pressure. After treatment the residual ethylene oxide is removed and then the polymer is usually blanketed by nitrogen and washed with air, for instance in several steps.

The invention provides also a method of producing the novel kit by coating an assembly consisting of a balloon catheter having a stent mounted on the balloon with a liquid coating composition containing a film forming polymer, and then curing the coating composition.

The process is generally carried out by dipping the assembly into a volume of the liquid composition, preferably so that the entire stent is immersed within the volume of liquid. Where only partial coating is required, the assembly maybe dipped to a depth whereby the portion to be desired is immersed in the liquid. Where it is desired to coat discrete areas of the surface, for instance discrete axially separated rings on the surface, it is convenient for the composition to be applied by spraying.

The liquid coating composition preferably comprises a film forming polymer and a solvent in which the polymer is dissolved or dispersed. Curing generally comprises removal of the solvent, for instance by evaporation under raised temperature and/or reduced pressure.

Curing preferably also comprises crosslinking of a crosslinkable polymer in the coating composition. Crosslinking maybe carried out before, during and/or after solvent removal. Crosslinking of a polymer which includes crosslinkable groups (as described above) involves subjecting the polymer to conditions under which the crosslinkable groups react to form inter-and intra molecular bonds. Such conditions generally involve heating the polymer, exposing it to incident actinic radiation and/or to moisture or gaseous crosslinking agents. Such agents may include ethylene oxide.

Preferably the method includes the step of sterilizing the coated assembly. Sterilization may be carried out simultaneously with curing and/or crosslinking steps. Sterilization may involve subjecting the coated assembly to raised temperature and/or pressure, irradiating the assembly and/or contacting the coated assembly with ethylene oxide. Preferably sterilization is carried out by contacting the coated assembly with ethylene oxide under the conditions described above in connection with the second aspect of the invention.

Most balloon catheters comprise a guidewire lumen so that the catheter can be run on a pre-positioned guidewire for navigation through the desired body lumens. In the present invention it may be desirable to coat the inside of the body lumen with the same type of coating as the exterior surface of the stent and balloon. The method therefore it maybe desirable to allow the coating composition to coat the guide wire lumen, for instance by leaving the lumen open during a dipping step and/or by directing liquid compositions through the lumen during a dipping or spraying process. Alternatively it maybe desired to avoid coating the guidewire lumen, for instance to avoid reducing the internal diameter of the lumen. In this case, the lumen may be blocked during the coating process using a suitable bung.

In the kit of the invention the coherent coating should have a thickness which avoids increasing the external diameter of the kit by an unacceptable amount, but which has adequate thickness to provide mechanical strength to improve retention of the stent by the desired amount. The thickness should not be so high as increase the pressure at which the balloon deploys the stent. The coating thickness, on the stent external surface, is preferably in the range 5 to 500 nm, most preferably in the range 10 to 200 nm, for instance in the range 20 to 100 nm. The coating may have the same thickness on the balloon and on the stent or may be thicker on the surface of the balloon.

The coating thickness maybe adjusted as desired by controlling the rheology of the liquid coating composition, for instance by controlling the concentration, by selecting suitable coating conditions, for instance in terms of temperature, number of coatings of liquid composition applied, or by selecting suitable drying conditions, for instance in terms of the conditions under which excess liquid coating composition is allowed to drain from the stent, as well as conditions of temperature and/or reduced pressure.

In the methods the coating composition preferably has a polymer concentration in the range 2 to 50 g/l, most preferably in the range 5 to 25 g/l, for instance in the range 10 to 20 g/l.

The solvent in the coating composition is, for instance, an alcohol (including glycol), ether, water, alkane or mixtures. Preferably the solvent consists of ethanol, optionally with glycol, mixed with water or with alkane.

The stent is generally formed from a metallic tube provided with openings to confer balloon expandability. Alternatively the stent may be formed from bent or braided wires. Preferred stents have a wall thickness in the range 0.5 to 2.5 mm, most preferably being at least 1000 times the thickness of the coating (average). Preferably the stent is formed from stainless steel. It will often already be provided with an overall coating of biocompatible material. The overall coating may be formed of the same or different polymer as the polymer in the coating. It suitable has a thickness such that the total polymer coating thickness including the coherent film is less than 500 nm thick, for instance less than 250 nm thick.

We have found that the provision of a polymer coating on the outside of the stent/balloon catheter assembly provides improved retention of the stent on the catheter when subjected to axially directed forces, without any deterioration in the ability of the stent to be deployed effectively. The coating does not adversely effect the burst pressures of the balloons, nor the pressures to which the balloons needed to be inflated to achieve stent deployment. Since the coatings are biocompatible, and indeed have already been approved for use for coating stents for long term implantation, the biocompatibility will not be compromised.

The invention is illustrated further in the following examples.

EXAMPLE 1

The polymer used for this example was simplified as described in WO-A-98130615, polymer 05. The polymer was formed from 2-(methacryloyloxyethyl)-2'-(trimethylammoniumethyl)phosphate inner salt: dodecyl methacrylate: 3-hydroxypropyl methacrylate: 3-trimethoxysilylpropyl methacrylate in molar ratios of 23:47:25:5. Solutions of the polymer were made up in ethanol at different polymer concentrations. The test assemblies comprised Divysio stents, with (unexpanded outer) diameter 1.6 mm, length 28 mm and wall thickness 0.914 mm, formed of stainless steel and provided with a biocompatible coating comprised of the same polymer as used in this example on all surfaces at a coating thickness of about 20-100 μm, mounted on a Nycomed Copan balloon catheter having a 30 mm balloon having an expanded diameter (at 6 atm ($6 \times 10^5$ Pa)) of 3.5 mm. The stents were crimped onto the balloons of the balloon catheters using a standard crimping device with jaws of 0.036 in (0.91 mm) at a pressure of 80 psi ($5.5 \times 10^5$ Pa), all stents being mounted under the same conditions. The guidewire lumen of the balloon catheter was blocked using a suitably sized stylet.

The assembly of stent and balloon catheter was coated by dipping to a depth such that the stent was completely immersed in a volume of coating composition and then withdrawn vertically upwardly at a rate of 1.75-1.85 mm s$^{-1}$. The coated assemblies were dried and cured by heating to 70° C. for 4 hours.

The coated assemblies were then subjected to tests to determine the retention of the stent on the balloon and stent deployment. Different samples were used for the different tests.

The retention of the stent onto the balloon was measured by gripping the distall end of the catheter and drawing it through a 1.0 mm orifice, which is too small for the stent to pass through. The force is thus extent in a direction to shift the stent proximally. The retention values are set out in table 1 below, which shows the mean retention for 4 samples coated from different concentrations of polymer as specified, as well as the percentage increase in retention.

TABLE 1

| Polymer Concentration (g/l) | Mean Retention (N) | % increase in retention compared to control |
|---|---|---|
| Control | 2.93 | |
| 2.0 | 2.75 | −6.0 |
| 6.0 | 3.78 | 25.1 |
| 8.0 | 4.53 | 55.5 |
| 10.0 | 4.71 | 61.5 |

EXAMPLE 2

Assemblies coated as in example 1 with 10 g/l of the same polymer were subjected to tests of their deployment characteristics. The balloon catheter was inflated in 0.5 atmosphere (50 kPa) increments using a Bundenberg pressure gauge. The results of the individual tests are reported in table 2.

For each of the stents, there was gradual, immediate and even detachment of the stent from the balloon at full deployment. Following deployment there was free movement of the balloon from the stent for each of the samples. In no instances does the balloon burst during deployment.

TABLE 2

| Stent ID | Deployment Pressure (Atm) | Deployment Extent |
|---|---|---|
| 1 | 1.0 | a |
| | 1.5 | c |
| | 2.0 | e |
| 2 | 1.0 | b |
| | 1.5 | c |
| | 2.0 | e |
| 3 | 1.0 | b |
| | 1.5 | c |
| | 2.0 | d |
| | 2.5 | e |
| 4 | 1.0 | b |
| | 1.5 | c |
| | 2.0 | d |
| | 2.5 | e |
| 5 | 1.0 | a |
| | 1.5 | c |
| | 2.0 | d |
| | 2.5 | e |
| 6 | 1.0 | a |
| | 1.5 | c |
| | 2.0 | d |
| | 2.5 | e |

Key
a: no change
b: slight inflation of the balloon
c: stent flared, balloon slightly inflated at end
d: partial inflation of the balloon, and flaring of stent end
e: immediate (within about 5s) full deployment The coated stents were also characterised for their total coating thickness using atomic force microscopy. This indicated the mean coating thickness for the stent of the kit of the invention is about 80 nm, whilst that of the starting stents is about 50 nm. The extra thickness from the coherent coating used in the invention over the mounted stent is thus believed to be about 30 nm.

The specification for the balloon catheter requires that the stent should fully deploy at 8 atmospheres or less. The results taken as a whole indicate that each sample deploys satisfactorily. In combination with the results of example 1, this shows that the overcoating increases retention of the stent without adversely effecting the deployment characteristics.

EXAMPLE 3

Further assemblies of stents mounted on balloon catheters were coated using the 10 g/l polymer composition in ethanol, dried and cured using the same conditions as in example 1. In the example the coated assemblies were sterilized using a ethylene oxide sterilization cycle in which a small amount of steam is introduced into the chamber of the sterilizing device followed by a higher amount of ethyleneoxide. The assemblies are maintained in contact with the gas for a period of 5 hours at a pressure of about 350 Pa and a temperature of 50 C. Following exposure to the gas the gas is removed by evacuating the chamber then the chamber is filled sequentially with nitrogen and then clean volumes of air in several steps.

The retention values were measured using a technique similar to that used in example 1, but in which the stent was subjected to a force to move is distally rather than proximally. The coated assemblies were compared with control, uncoated assemblies.

The results are shown in table 3 below.

TABLE 3

| | Retention | | |
|---|---|---|---|
| Sample | Mean (n = 4)(N) | St. Dev(N) | % increase |
| Control | 1.55 | 0.19 | |
| Invention | 3.68 | 0.40 | 137 |

The results indicate that ethylene oxide treatment following curing leads to a greater increase in stent retention than coating and crosslinking by heating alone.

EXAMPLE 4

Further samples of the coated assemblies produced in example 3 were subjected to the deployment test described in example 1. Subsequent to the deployment tests, the balloons were and inflated up to failure. The balloons from the tests of example 3 were also subsequently inflated to failure.

The deployment tests indicate satisfactory deployment very similar to stents 3 to 6 in Example 1. Thus all tested samples were fully deployed at 2.5 atmosphere, within 5 seconds of the imposition of the pressure.

The results of the burst tests are shown in table 4. Samples 4.1 to 4.4 had been subjected to retention tests whilst samples 4.5 and 4.6 had been subjected to deployment tests.

TABLE 4

| Sample | Burst Pressure (atm/$10^5$ Pa) | Failure Mode |
|---|---|---|
| 4.1 | 18.0 | Pinhole |
| 4.2 | 20.0 | Axial split |
| 4.3 | 20.0 | Axial split |
| 4.4 | 18.0 | Pinhole |
| 4.5 | 19.7 | Axial split |
| 4.6 | 20.4 | Axial split |

The "pinhole" failures observed were caused by the piercing of the balloon during measurement of the retention values. It is considered unlikely that the pinholes in the balloons were caused by the overcoating. Since it is unlikely that the stent will be subjected to forces as high as those required to dislodge the stent from the balloon during normal use, it is believed that the pinholes in the balloons were caused by the overcoating. The average burst pressure of balloons having been used to deploy stents is about $20\text{-}22 \times 10^5$ Pa. The coating appears not to reduce this. In any event all pressures recorded at failure were higher than the minimum pressure required in a product specification which is 16 atm ($10^5$ Pa).

EXAMPLE 5

Further sampling of the stent/catheter assembly used in the previous examples were coated with a copolymer of 2-methacryloyloxyethyl-2'-trimethyl ammoniumethyl phosphate inner salt:dodecyl-methacrylate 1:2 (molar) synthesised substantially as in example 1 of WO-A-9301221) from a 10 g/l solution in ethanol. The coated assemblies (without prior sterilisation) were subjected to the retention test. The retention rates were about 60% higher than those of the control.

EXAMPLE 6

Overcoating with Alternative Polymers

Alternative polymer overcoating systems were evaluated using 15 mm DivYsio stents that had been crimped onto nylon 6,6 filament (1 mm diameter, Goodfellows) as a model for the nylon balloon catheter. This model is formed of the same polyamide as the balloon and has approximately the same diameter. The stent/filament combination was dip-coated at 3 mm/sec into a solution of the polymer under study dissolved in an appropriate solvent and left to air dry for 30 minutes. The sample was then oven dried at 70 C overnight prior to determining the extent of retention. The retention values were determined using a technique similar to that used in example 1.

TABLE 5

| Polymer/Sample | Solvent Concentation | Mean (n = 6) (N) | St. Dev (N) | % Increase |
|---|---|---|---|---|
| Non Overcoated Control | — | 0.0725 | 0.023 | — |
| PC Coated (Example 1) | 10 g/L Ethanol | 2.967 | 0.557 | 3992 |
| PEG 10,000 (Aldrich) | 10 g/L (90:10) Ethanol:water | 0.665 | 0.158 | 817 |
| TECOFLEX (Thermedics) | 10 g/L THF | 0.158 | 0.066 | 118 |
| Hydroxyethylcellulose (Cellusize, Union Carbide) | 1 g/L water | 0.102 | 0.034 | 40 |

The results show that similar increases in retention can be obtained using a variety of polymer samples, including water-soluble systems, biological macromolecules and synthetic polymers.

The invention claimed is:

1. A kit comprising a balloon catheter comprising a balloon at or near its distal end, and a stent mounted on the balloon, wherein the exterior surface of the balloon and stent are provided with a coherent coating comprising a film-forming polymer, in which the polymer is formed from ethylenically unsaturated monomers including a zwitterionic monomer of the general formula I:

YBX      I wherein

B is a straight or branched alkanediyl, alkyleneoxaalkylene or alkylene oligo-oxaalkylene chain optionally containing one or more fluorine atoms up to and including perfluorinated chains or, if X or Y contains a terminal carbon atom bonded to B, a valence bond;

X is a zwitterionic group; and

Y is an ethylenically unsaturated polymerizable group selected from the group consisting of

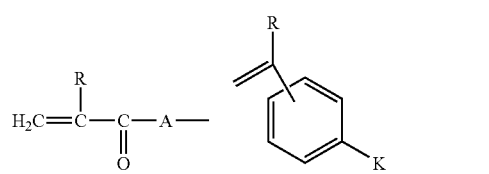

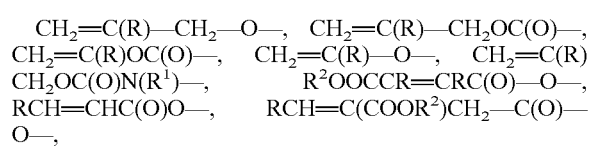

$CH_2$=$C(R)$—$CH_2$—O—,   $CH_2$=$C(R)$—$CH_2OC(O)$—,
$CH_2$=$C(R)OC(O)$—,   $CH_2$=$C(R)$—O—,   $CH_2$=$C(R)$
$CH_2OC(O)N(R^1)$—,      $R^2OOCCR$=$CRC(O)$—O—,
$RCH$=$CHC(O)O$—,      $RCH$=$C(COOR^2)CH_2$—$C(O)$—O—,

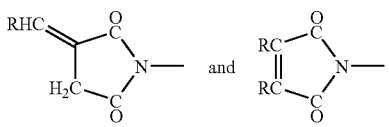

wherein:
R is hydrogen or a $C_1$-$C_4$ alkyl group;
$R^1$ is hydrogen or a $C_1$-$C_4$ alkyl group or $R^1$ is —B—X where B and X are as defined above; and
$R^2$ is hydrogen or a $C_{1-4}$ alkyl group;
A is —O— or —$NR^1$—;
K is selected from the group consisting of —$(CH_2)_pOC(O)$—, —$(CH_2)_pC(O)O$—, —$(CH_2)_pOC(O)O$—, —$(CH_2)_pNR^3$—, —$(CH_2)_pNR^3C(O)$—, —$(CH_2)_pC(O)NR^3$—, —$(CH_2)_pNR^3C(O)O$—, —$(CH_2)_pOC(O)NR^3$—, —$(CH_2)_pNR^3C(O)NR^3$— (in which the groups $R^3$ are the same or different), —$(CH_2)_pO$—, —$(CH_2)_pSO_3$—, and, in combination with B, a valence bond p is from 1 to 12; and
$R^3$ is hydrogen or a $C_1$-$C_4$ alkyl group.

2. A kit according to claim 1 in which X is a group having the general formula III

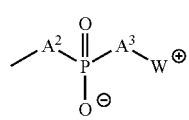

III in which the moieties $A^2$ and $A^3$, which are the same or different, are selected from the group consisting of —O—, —S—, —NH— and a valence bond, and $W^+$ is a group comprising a cationic group selected from the group consisting of ammonium, phosphonium and sulphonium cationic groups and a group linking the anionic and cationic moieties which is a $C_{1-12}$-alkanediyl group.

3. A kit according to claim 2 in which $A^2$ and $A^3$ are each —O—.

4. A kit according to claim 2 in which $W^+$ is a group of formula

—$W^1$—$N^+R^9{}_3$, —$W^1$—$P^+R^{10}{}_3$, —$W^1$—$S^+R^{10}{}_2$ or
—$W^1$—$Het^+$ in which:

$W^1$ is selected from the group consisting of alkanediyl of 1-6 carbon atoms optionally containing one or more ethylenically unsaturated double or triple bonds, disubstituted-aryl(arylene), alkylene arylene, arylene alkylene, alkylene aryl alkylene, cycloalkanediyl, alkylene cycloalkyl, cycloalkyl alkylene and alkylene cycloalkyl alkylene, which group $W^1$ optionally contains one or more fluorine substituents and/or one or more functional groups; and
either the groups $R^9$ are the same or different and each is selected from the group consisting of hydrogen, alkyl of 1 to 4 carbon atoms and aryl, or two of the groups $R^9$ together with the nitrogen atom to which they are attached form an aliphatic heterocyclic ring containing from 5 to 7 atoms, or the three groups $R^9$ together with the nitrogen atom to which they are attached form a fused ring structure containing from 5 to 7 atoms in each ring, and optionally one or more of the groups $R^9$ is substituted by a hydrophilic functional group, and the groups $R^{10}$ are the same or different and each is $R^9$ or a group $OR^9$, where $R^9$ is as defined above; or
Het is an aromatic nitrogen-, phosphorus- or sulphur-containing ring.

5. A kit according to claim 1 in which X is a group having the general formula IV:

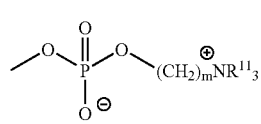

IV where the groups $R^{11}$ are the same or different and each is hydrogen or $C_{1-4}$ alkyl, and m is from 1 to 4.

6. A kit according to claim 5 in which the groups $R^{11}$ are the same.

7. A kit according to claim 6 in which the groups $R^{11}$ are all methyl.

8. A kit according to claim 1 in which the ethylenically unsaturated monomers include a surface binding monomer having the general formula II $Y^1R^4$   II wherein $Y^1$ is selected from the group consisting of

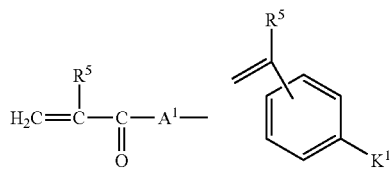

$CH_2=C(R^5)$—$CH_2$—O—,   $CH_2=C(R^5)$—$CH_2OC(O)$—,   $CH_2=C(R^5)OC(O)$—,   $CH_2=C(R^5)$—O—,   $CH_2=C(R^5)CH_2OC(O)N(R^6)$—,   $R^7OOCCR^5=CR^5C(O)$—O—,   $R^5CH=CHC(O)O$—,   $R^5CH=C(COOR^7)CH_2$—$C(O)$—O—,

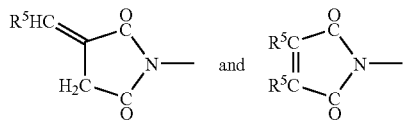

wherein:
$R^5$ is hydrogen or a $C_1$-$C_4$ alkyl group;
$R^6$ is hydrogen or a $C_1$,—$C_4$ alkyl group or $R^6$ is $R^4$;
$R^7$ is hydrogen or a $C_{1-4}$ alkyl group;
$A^1$ is —O— or —$NR^6$—; and
$K^1$ is selected from the group consisting of —$(CH_2)_qOC(O)$—, —$(CH_2)_qC(O)O$—, —$(CH_2)_qOC(O)O$—, —$(CH_2)_qNR^8$—, —$(CH_2)_qNR^8C(O)$—, —$(CH_2)_qC(O)NR^8$—, —$(CH_2)_qNR^8C(O)O$—, —$(CH_2)_qOC(O)NR^8$—, —$(CH_2)_qNR^8C(O)NR^8$— (in which the groups $R^8$ are the same or different), —$(CH_2)_qO$—, —$(CH_2)_qSO_3$—, and a valence bond q is from 1 to 12;

and $R^8$ is hydrogen or a $C_1$-$C_4$ alkyl group;

and $R^4$ is a surface binding group, selected from hydrophobic groups, ionic groups, reactive groups capable of forming covalent bonds with surface functional groups on the surface of the tube and crosslinkable groups capable of forming intermolecular crosslinks, optionally in conjunction with curing agents.

9. A kit according to claim 1 in which the ethylenically unsaturated monomers comprise a) a zwitterionic monomer of the general formula

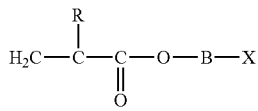

in which

R is hydrogen or methyl;

B is $C_{2-6}$-alkanediyl; and

X is a group having the general formula IV:

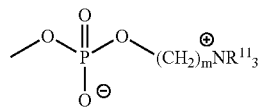

IV where the groups $R^{11}$ are the same or different and each is hydrogen or $C_{1-4}$ alkyl, and m is from 1 to 4;

b) a surface binding monomer of the general formula

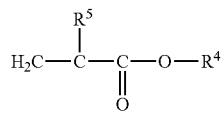

in which $R^5$ is hydrogen or methyl; and $R^4$ is selected from the group consisting of straight and branched alkyl, alkoxyalkyl and oligoalkoxyalkyl groups comprising 6 to 24 carbon atoms, unsubstituted or substituted by one or more fluorine atoms; and c) a silyl group containing monomer of the general formula

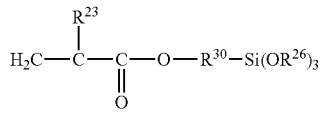

in which $R^{23}$ is hydrogen or methyl;

$R^{30}$ is a $C_{2-24}$ alkanediyl group; and each $R^{26}$ is methyl or ethyl.

10. A kit according to claim 9 in which $R^4$ is selected from the groups consisting of straight and branched alkyl, alkoxyalkyl and oligoalkoxyalkyl groups comprising 6 to 24 carbon atoms, unsubstituted or substituted by one or more fluorine atoms and containing one or more carbon-carbon double or triple bonds.

* * * * *